United States Patent [19]

Sampson et al.

[11] 4,447,984

[45] May 15, 1984

[54] PROCESS FOR OBTAINING IMPROVED YIELDS FROM PLANTS

[76] Inventors: Michael J. Sampson, 21, The Avenue, Chichester, Sussex; Neville Hutchings, The Station, Edwinstowe, Mansfield, Notts., both of England

[21] Appl. No.: 270,516

[22] PCT Filed: Oct. 6, 1980

[86] PCT No.: PCT/GB80/00155

§ 371 Date: Jun. 8, 1981

§ 102(e) Date: Jun. 8, 1981

[87] PCT Pub. No.: WO81/00955

PCT Pub. Date: Apr. 16, 1981

[30] Foreign Application Priority Data

Oct. 13, 1979 [GB] United Kingdom ............... 7935652
May 2, 1980 [GB] United Kingdom ............... 8014695
Jul. 11, 1980 [GB] United Kingdom ............... 8022810
Jul. 30, 1980 [GB] United Kingdom ............... 8024986
Aug. 12, 1980 [GB] United Kingdom ............... 8026246

[51] Int. Cl.³ ............................................. A01G 1/00
[52] U.S. Cl. ................................ 47/58; 47/DIG. 11; 71/92
[58] Field of Search ............... 47/58, DIG. 11; 71/92

[56] References Cited

U.S. PATENT DOCUMENTS

| | | | |
|---|---|---|---|
| 2,262,454 | 11/1941 | Flenner | 47/58 X |
| 2,864,681 | 12/1958 | Nickell | 71/2.5 |
| 3,118,753 | 1/1964 | Shive et al. | 71/2.5 |
| 3,156,554 | 11/1964 | Tolbert | 71/2.7 |
| 3,269,057 | 8/1966 | Heineman | 47/58 |
| 3,332,959 | 7/1967 | Braunholtz et al. | 260/296 |
| 3,395,009 | 7/1968 | Oettel et al. | 71/76 |
| 3,458,627 | 7/1969 | Daudin et al. | 424/170 |
| 3,493,361 | 2/1970 | Nickell et al. | 71/121 |
| 3,592,910 | 7/1971 | Clark et al. | 424/300 |
| 3,728,817 | 4/1973 | Huey et al. | 47/58 |
| 3,920,443 | 11/1975 | Drewe et al. | 71/94 |
| 4,046,552 | 9/1977 | Davies et al. | 71/92 |
| 4,075,005 | 2/1978 | Knowles et al. | 71/94 |
| 4,212,664 | 7/1980 | Takeuchi et al. | 71/94 |

FOREIGN PATENT DOCUMENTS

| | | |
|---|---|---|
| 532117 | 1/1958 | Belgium . |
| 521753 | 3/1931 | Fed. Rep. of Germany . |
| 2041936 | 12/1971 | Fed. Rep. of Germany . |
| 2460592 | 2/1975 | Fed. Rep. of Germany . |
| 2702096 | 7/1977 | Fed. Rep. of Germany . |
| 2820359 | 11/1978 | Fed. Rep. of Germany . |
| 950170 | 9/1949 | France . |
| 1433576 | 2/1966 | France . |
| 2143806 | 6/1972 | France . |
| 2251262 | 11/1974 | France . |
| 2255015 | 12/1974 | France . |
| 2358831 | 2/1978 | France . |
| 108029 | 9/1974 | German Democratic Rep. . |
| 639937 | 7/1950 | United Kingdom . |
| 679917 | 9/1952 | United Kingdom . |
| 955685 | 4/1964 | United Kingdom . |
| 1207787 | 10/1970 | United Kingdom . |
| 1356018 | 6/1974 | United Kingdom . |
| 1424889 | 2/1976 | United Kingdom . |
| 1491856 | 11/1977 | United Kingdom . |
| 1498004 | 1/1978 | United Kingdom . |
| 424547 | 10/1974 | U.S.S.R. . |
| 641949 | 1/1979 | U.S.S.R. . |
| 658128 | 4/1979 | U.S.S.R. . |

*Primary Examiner*—Robert E. Bagwill
*Attorney, Agent, or Firm*—Maky, Renner, Otto & Boisselle

[57] ABSTRACT

Crops are treated with a composition which prevents the premature opening of seed pods.

6 Claims, No Drawings

PROCESS FOR OBTAINING IMPROVED YIELDS FROM PLANTS

This invention relates to the treatment of plants and compositions for such treatment.

A large number of leguminous plants, such as oilseed rape, peas and beans, are grown principally for their seed. These seeds are formed in pods which, on ripening, split along their longitudinal axes. As a result, the seeds fall onto the ground. Where such crops are mechanically harvested, the problem of seed lost by premature pod splitting can be a serious economic problem. Oilseed rape, which is invariably harvested mechanically, has a strongly marked tendency for its pods to split either just before or during harvesting.

In addition to leguminous crops, the seeds or seed-bearing heads or bodies of ornamental plants, cereals (especially barley), grasses grown for seed production and vegetables being raised for seed all suffer from premature loss of seed before harvesting.

In accordance with the present invention, the loss of seed through premature release or scattering is controlled by the treatment of the crop plant, after seed body formation, with a coating or layering substance that will prevent the detachment of the seed or seed body or will control the splitting of pods or seed-bearing bodies. The treatment is usually carried out not more than fifteen days before the crop is ready for harvesting, which distinguishes the treatment of this invention from that in prior Applications Number PCT/GB 80/00016, European 8032353.0 and UK 8,022,640, in which coating agents are usually applied at least fifteen days before harvest.

Substances that may be used for this purpose must not affect the subsequent germination of seeds that are destined to be planted. Of particular value are a group of pinolene products based on di-1-p-menthene under a variety of trade names including Miller Aide, Miller Gard, Nu-Film P, Nu-Film 17 and Vapor Gard. These products, which contain di-1-p-menthene and certain of its polymers, further polymerize to form a film, and such further polymerization may take place or even be induced before application. Other monoterpenes of formula $C_{10}H_{16}$, which correspond to two isoprene units, can also be used.

Pinolenes are naturally occurring substances and are both expensive and in short supply in relation to possible agricultural needs. It is therefore useful to extend them by using them in combination with other coating agents. Such compounds or mixtures of coating agents (which may be polymerized before application) can show properties unlike those of their individual components. The mixtures contain from 2 to 10 coating agents, one or more of which is preferably a pinolene compound although mixtures without such compounds may be used.

Apart from the monoterpenes mentioned, the following compounds are suitable, though this is not an exhaustive list:

1. Terpene hydrocarbons of the elementary composition $C_{15}H_{24}$ (sesquiterpenes)
2. Terpene hydrocarbons of the elementary composition $C_{20}H_{32}$ (diterpenes)
3. Terpene hydrocarbons of the elementary composition $C_{30}H_{48}$ (triterpenes)
4. Terpenes having 40 carbon atoms (tetraterpenes)
5. Bicyclic and tricyclic monoterpenes and their derivatives (e.g. oxygenated derivatives) such as $\alpha$ and $\beta$ pinene, d-camphor, d-borneol, d-tanacetone, $\beta$-thujone, d-$\Delta^3$-carene
6. Terpene resins (compounded with or without natural or synthetic rubbers)
7. Gum turpentine
8. Sulphate of turpentine
9. Wood turpentine
10. Pineoils
11. Terpineols
12. Alkyd Resins, Non-oxidizing—e.g. those of the castor oil, coconut oil, hydrogenated castor oil, lauric acid, oil-free, saturated acid and synthetic fatty acid types
13. Alkyd Resins, Oxidizing—e.g. acrylic-resin-modified, dehydrated castor oil types, epoxide-resin-modified, isophthalic-acid-based types, linoleic-rich oil type, linseed oil types, linseed oil/dehydrated castor oil types, linseed oil/soya bean oil types, linseed oil/tung oil types, maleic-resin-modified, marine oil types, phenolic-resin-modified, rosin-modified, safflower seed oil types, silicone-resin-modified, soya bean oil types, soya bean oil/tung oil types, styrenated types, sunflowerseed oil types, tall oil types, tobaccoseed oil types, unmodified types, vinyltoluene-modified and water-soluble types
14. Benzoguanamine resins
15. Styrene polymers and copolymers, e.g. polystyrene and styrene/maleic anhydride and butadiene/styrene copolymer resins
16. Carbamide resins
17. Copal ester resins
18. Coumarone-indene resins
19. Cresylic resins
20. Epoxy resins—e.g. dehydrated castor oil types, linseed oil types, linseed oil/rosin types, phenolic-resin-modified, soya bean oil types, styrenated types, vinyltoluene-modified, unmodified types, epikote 828 and epikote 1001
21. Epoxide melamine condensates
22. Epoxide phenolic condensates
23. Ester gums
24. Fumaric resins
25. Furan resins
26. Ketone resins
27. Maleic resins
28. Melamine resins—e.g. butylated types, hexamethoxymethyl types and formaldehyde condensates
29. Metallic rosinates—e.g. calcium or zinc resinates, zinc/calcium mixtures both rosin or modified rosin
30. Phenolic resins and modified phenolic resins—e.g. phenol/aldehyde resole condensates adducted to rosin or modified rosin, as well as phenol/formaldehyde resins
31. Phenoxy resins
32. Polybutadiene resins
33. Polybutene resins
34. Polycarbonate resins
35. Polyisobutylene resins
36. Polyester resins—e.g. polyacrylate and polymethacrylate ester resins
37. Polysulphide resins
38. Polyurethane resins—e.g. modified types and oil-modified types
39. Polyvinyl acetal resins
40. Polyether resins—e.g. polyvinyl ether resins 41. Polyvinyl formal resins
42. Rosin derivatives—e.g. esters of rosin, copal, rosin acids or rosin modified by hydrogenation, polymerization isomerization or disproportionation with glycerol, pentaerytbritol or other polyhydric alcohols
43. Maleic/fumaric condensate resins—e.g. maleic or fumaric acid/anhydride adducts on rosin or modified rosins, their esters with glycerol, pentaerythritol or other polyhydric alcohols
44. Silicone resins and polymers
45. Urea resins—e.g. urea-formaldehyde
46. Xylene-formaldehyde resins
47. Natural gums/resins—e.g. accoroides, arabic, benzoin, copals, damar, elemi, gamboge, karaya, mastic, rosin, sandarac, shellac and tragacanth
48. Acrylic polymers and copolymers—e.g. polyacrylic acid, polyacrylamide, polyacrylonitrile, poly(methyl methacrylate) and poly(ethyl acrylate/butyl acrylate)
49. Cellulose ethers—e.g. hydroxyethyl cellulose and sodium carboxymethyl cellulose
50. Cellulose esters—e.g. methyl cellulose
51. Hydrocarbon resins—e.g. petroleum resins
52. Polyamide resins
53. Rubbers—e.g. natural rubber, butyl rubber, nitrile rubber, polychloroprene, rubber/oil emuline and polyurethane rubber and cyclized rubber resins
54. Vinyl polymers and copolymers other than those already mentioned—e.g. poly(vinyl acetate), poly(vinyl alcohol), poly(vinyl butyral), poly(vinyl pyrrolidone), poly(vinyl acetate/vinyl chloride) and poly(vinyl acetate/acrylate) and
55. Natural drying oils—e.g. linseed oil and tung oil and mixtures of them.

Such substances may be used at rates of from one fluid ounce to ten pints per acre (70 to 14000 ml per hectare) applied in three to one hundred gallons of water per acre (33.7 to 1120 liters per hectare) of crop. It can be useful to include in the spray preparation a surfactant or wetting agent. Such surfactants include but are not limited to:

1. alkyl phenolethylene oxide condensate
2. Triton X100
3. Cittowet (trade mark of BASF)
4. alkylated aromatic sodium suphonate
5. amine salts or suphated fatty alcohols and
6. tall oil The coating or layering substance for checking seed loss hereinbefore described may conveniently be applied mixed with a chemical desiccant, which is a substance that promotes the drying out of the plant to facilitate harvest and/or produces the harvested yield in better condition for storage. Such desiccants include but are not limited to the bipyridilium herbicide diquat (sold under the trade mark Reglone by ICI Ltd) and dinoseb. Diquat has been found especially useful to facilitate the harvesting or oilseed rape and is widely used for this purpose.

The use of the coating or layering substance hereinbefore described for preventing seed loss can result in an increase in the harvested seed yield of oilseed rape while the treatment of this crop with diquat can also result in an increase in the harvested seed yield. These two yield-improving factors act in different ways and, when used together, e.g. when applied either in tank mixtures or separately within seven days of one another, can give an increase in a harvested seed yield that is greater than the sum of the effect of each additive singly.

In another aspect the use of the layering or coating substance hereinbefore described for controlling seed loss can enable a lower rate of desiccant to be applied to an oilseed rape crop or other suitable crop. Because pod splitting is checked the process of desiccation is less demanding, and amounts of desiccant can be reduced by some 30% over what would normally be recommended.

As is well known, certain weeds in a ripening crop that check ripening or interfere with harvesting must be controlled shortly before harvesting. An example of this is the control of sterile brome grass in a cereal crop. Applying a herbicide in conjunction with a composition in accordance with the present invention can be used to control such weeds, either by destroying the herbage or by destroying or preventing production of weed seeds. Where the weed is green and alive at the time when the cereal or other crop plant has commenced the ripening process then the crop may be treated with a herbicide, for example glyphosate, that would kill or seriously damage a green (living) crop such as wheat or barley. By its use in conjunction with a coating agent in accordance with the present invention, the activity of the herbicide on the weed may be enhanced, while by checking or delaying the entry of the herbicide into the crop the specificity or crop safety of the herbicide is improved. With each additional day of ripening, the crop becomes less susceptible to damage by a herbicide while, since less herbicide is taken into the riper crop, there is a reduction with time in the tendency of the crop to accumulate undesirable residues of the pesticide that could result in the crop being less suitable for human or for animal consumption and its value for seed or malting being reduced since the presence of herbicide in the grain can reduce or slow down germination. The use of a coating agent in accordance with the present invention can make it possible to feed the grain to livestock without further processing and can enhance its value for seed or malting. Delaying the penetration of the herbicide while the crop is ripening before the weed is therefore a desirable objective.

A further value in the use of the coating agent during the ripening period is that, since the loss of seed may be checked, it becomes possible to leave the harvest in the field for a somewhat longer ripening period and thus reduce drying costs.

The tendency of the crop ripening process to be impeded by the coating agent can usefully be overcome by the inclusion of a wetting (surfactant) agent such as 'Agral' (alkylphenol ethylene oxide condensate). When the wetting agent is used in combination with the coating agent and glyphosate, its herbicidal activity can be enhanced by an amount over and above that which is obtainable by the use of either additive considered separately.

The coating agent used in accordance with the present invention can be used alone or in conjunction with a fungicide to prevent the development of fungal organisms on the pod or seed-bearing body (such as the ear of a cereal plant) and/or the penetration of micro-organisms into the pod to cause loss of yield and/or quality as in the case of "staining" of peas. The control of ear disease in cereals, especially during the ripening process, at which time they are particularly susceptible to cladosporium (sooty mould) disease, may be controlled.

The coating agent may also serve as a physical barrier to the establishment of the fungal organism on the pod or seed-bearing body or seed including the sealing of a pod or seed-bearing structure against the penetration of micro-organisms.

Similarly an insecticide may be incorporated with the coating agent to control pre-harvest insect pests such as cereal aphids and midges. The coating agent, by forming a water-repellent layer over the pod or other reproductive body, serves to speed its drying and hence to check micro-organism development, which requires moisture in which to flourish.

The coating agent may also be used to bind the fungicide and/or insecticide to the grain of cereal plants before harvesting to preserve them from post-harvest fungal and/or insect attack. This may encompass the use of such agricultural pesticides in a seed crop such that fungal and/or insect attack on the seed following planting is reduced.

Examples of fungicides and insecticides that may be used either by incorporation with the coating agent or by use in tank mixture with the coating agent include, but are not limited to, the following:

| | |
|---|---|
| benomyl | ethirimol |
| Bordeaux mixture | fenitrothion |
| captafol | fentin hydroxide |
| captan | malathion |
| carbendazim | mancozeb |
| carboxin | maneb |
| chlorothalonoil | pirimiphos-methyl |
| cyhexatin | pyrethrum |
| demephian | streptomycin |
| demeton-s-methyl | sulphur |
| diazinon | thiabendazole |
| dichlorvos | triadimephon |
| dicofol | thiophanate-methyl |
| dimethirimol | tridemorph |
| dimethoate | triforine |
| dithiocarbamate fungicide | zineb |
| dodine | thiram |

The foregoing are the trivial names from Pesticide Index. Herbicides or desiccants may additionally be included in combination with the fungicide and/or insecticide.

A further advantage of a water-repellent coating layer over a pod or seed-bearing body such as a cereal ear is the control or sprouting or premature seed germination. This can be a particular problem in both oilseed rape and cereals. In the case of barley, biochemical changes produced in response to germination (and hence water imbibition by the seed during or after ripening) will lower the malting quality or even render the grain unsuitable for this purpose and hence of lower value.

By acting as a semi-permeable membrane the polymeric coating agents can also prevent re-absorption of moisture after harvest (although not impeding the ripening process).

The coating agent may be used to prevent the penetration of an agricultural chemical with which it is applied, for example diquat or paraquat desiccants, through the seed coat of plants such as oilseed rape and soya. Thus, wherever the edible part of the crop is contained within a non-edible structure it is preferable that an applied agricultural chemical be contained on this and not penetrate it and thereby increase the residues or levels of undesirable agricultural chemicals within the seed or other edible portion of the crop.

The coating agent may also be used in combination with a bird repellent. This can be of particular importance in sunflower.

In addition to treating pods or seed-bearing bodies, the coating agent, with or without a further agricultural chemical or chemicals, may be used for treating other larger reproductive/storage bodies, such as the ear of maize, which may be treated by dipping or spraying post harvest.

The following experimental data show the effect of various coating agents in the control of pod shatter in oilseed rape. The agent was applied at the time when the pods were turning yellow and pliable, which is also the recommended time for applying the desiccant diquat.

Dried, hand harvested pods were subjected to a standard treatment of dropping and shaking in bags sufficient to induce 95% shatter in a control sample. Other samples were then similarly treated. In this test therefore a reduction in pod shatter from 95% to 90% represents a 100% increase in unbroken pods.

| | % Pod Shatter | Application Rate (liters per hectare) |
|---|---|---|
| Control | 95 | — |
| A. Polyterpene Resin (Nitrez) | 78 | 0.7 |
| B. Hydrogenated methyl ester of rosin (100%) (Hercolyn D) | 56 | 0.7 |
| C. Acrylic polymer emulsion (50%) (VINACRYL 4001) | 80 | 1.4 |
| D. Styrene Acrylic co-polymer emulsion (Vinacryl 7191) | 75 | 1.4 |
| E. Low molecular weight urea formaldehyde-resin (Casco 731) | 92 | 1.4 |
| F. Ester resin in oxital (90%) | 90 | 0.7 |
| G. Di-1-p-menthene | 40 | 0.7 |
| H. Di-1-p-menthene | 35 | 0.7 |

Except in the case of (H), where application was made in tank mixture with the desiccant glyphosate (Roundup), all applications were made in tank mixture with the desiccant diquat (Reglone) at 2½ pints per acre (3.5 liters per hectare) using a spray volume of 50 gallons per acre (560 liters per hectare). Control plants were treated with diquat but received no coating agent.

Whole pods taken from the samples described in the foregoing table before induction of shattering were placed in a polythene bag with sufficient water to induce moistening and growth of fungal moulds. After ten days they were scored from 0 (no growth) to 10 (the level of mould development on the control pods) and the results were as follows:

| | Infestation Score |
|---|---|
| Control | 10 |
| A. Polyterpene Resin (Nitrez) | 7 |
| B. Hydrogenated methyl ester of rosin (100%) (Hercolyn D) | 7 |
| G. Di-1-p-menthene (applied with diquat) | 5 |

The foregoing data demonstrate that application of a coating agent can control pod shatter to a marked extent, with concurrent reduction in growth of fungal moulds.

Further experiments were carried out on peas and beans to demonstrate that levels of the pesticide dimethoate (which was used because it can readily be assayed accurately and specifically) were diminished by application of a coating agent in accordance with the present invention.

All samples were treated with the standard commercial amounts of Reglone (diquat)+Agral wetting agent viz 3 pints of Reglone plus 6.4 fl oz of Agral per acre (4.2 liters of Reglone plus 450 ml of Agral per hectare) the spray volume being 40 gallons per acre (450 liters per hectare). The amount of di-1-p-menthene was 0.7 liters/hectare (0.5 pints/acre) and of dimethoate 40% (w/v) was 840 ml per hectare (standard commercial rate).

| | Interval between spraying & harvest (days) | ppm Dimethoate in seed |
| --- | --- | --- |
| Peas (Little Marvel) | | |
| (a) Control* | 6 | 0.009 |
| Dimethoate + Di-1-p-menthene | 6 | 0.037 |
| Dimethoate | 6 | 0.049 |
| Broad Beans (Express) | | |
| (a) Control* | 6 | 0.004 |
| Dimethoate + Di-1-p-menthene | 6 | 0.031 |
| Dimethoate | 6 | 0.10 |
| (b) Control* | 10 | 0.006 |
| Dimethoate + Di-1-p-menthene | 10 | 0.11 |
| Dimethoate | 10 | 0.15 |

All results are corrected for the average recovery
*No dimethoate applied

We claim:

1. A method for reducing or preventing premature release or scattering of seed due to splitting of seed-bearing bodies comprising applying to plants bearing said seed-bearing bodies, not more than fifteen days before harvest, an effective amount of a composition comprising di-1-p-menthene and/or polymeric di-1-p-menthene to provide a semi-permeable coating on said seed-bearing bodies.

2. The method of claim 1 wherein said composition is an aqueous composition.

3. The method of claim 1 wherein said composition further comprises an effective amount of a desiccant to dry said plants sufficiently to facilitate the harvesting of said plants.

4. The method of claim 3 wherein said dessicant is diquat.

5. The method of claim 1 wherein said composition comprises a surfactant.

6. The method of claim 1 wherein said composition comprises a herbicide.

* * * * *